United States Patent
Rand et al.

(10) Patent No.: US 6,360,739 B1
(45) Date of Patent: Mar. 26, 2002

(54) DISPENSER WITH DOSES COUNTER

(75) Inventors: Paul Kenneth Rand, Redhill; Peter John Brand, Royston; James William Godfrey, Hertfordhire, all of (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/445,659

(22) PCT Filed: Jun. 8, 1998

(86) PCT No.: PCT/EP98/03378

§ 371 Date: Mar. 31, 2000

§ 102(e) Date: Mar. 31, 2000

(87) PCT Pub. No.: WO98/56445

PCT Pub. Date: Dec. 17, 1998

(30) Foreign Application Priority Data

Jun. 10, 1997 (GB) .............................. 9711889
Oct. 16, 1997 (GB) .............................. 9721875

(51) Int. Cl.⁷ .............................................. A61M 16/00
(52) U.S. Cl. ......................... 128/200.23; 128/203.12; 128/200.18; 128/200.14; 128/203.23
(58) Field of Search ................... 128/203.12, 200.18, 128/200.23, 200.14, 203.15, 203.19, 203.23; 222/38, 36, 162

(56) References Cited

U.S. PATENT DOCUMENTS

| 4,817,822 A | * | 4/1989 | Rand et al. ................... 222/38 |
| 5,069,204 A | | 12/1991 | Smith et al. |
| 5,263,475 A | | 11/1993 | Aletermatt et al. |
| 5,349,945 A | * | 9/1994 | Wass et al. ............ 128/200.23 |
| 5,411,173 A | | 5/1995 | Weinstein |
| 5,482,030 A | | 1/1996 | Klein |
| 5,522,378 A | * | 6/1996 | Ritson et al. .......... 128/200.14 |
| 5,544,647 A | | 8/1996 | Jewett et al. |
| 5,622,163 A | | 4/1997 | Jewett et al. |
| 5,718,355 A | | 2/1998 | Garby et al. |
| 5,826,571 A | | 10/1998 | Casper et al. |
| 6,029,659 A | * | 2/2000 | O'Connor .............. 128/203.12 |
| 6,142,339 A | | 11/2000 | Blacker et al. |
| 6,161,724 A | | 12/2000 | Blacker et al. |

FOREIGN PATENT DOCUMENTS

| EP | 0 280 104 A | 8/1988 |
| WO | 92/17231 | 10/1992 |
| WO | WO 93 24167 A | 12/1993 |
| WO | 94/14492 | 7/1994 |
| WO | 96/16686 | 6/1996 |
| WO | WO 96 39337 | 12/1996 |
| WO | 99/36115 | 7/1999 |

* cited by examiner

Primary Examiner—John G. Weiss
Assistant Examiner—Mital Patel
(74) Attorney, Agent, or Firm—Christopher P. Rogers

(57) ABSTRACT

There is provided a dispenser suitable for dispensing medicament, particularly medicament for use in the treatment of respiratory disorders. The dispenser comprises a housing (1) having a support (5), a container (2), locatable within said housing (1), having an outlet (3), wherein said container (2) dispenses through said outlet (3) in response to movement of the container (2) relative to the housing (1) and an actuation indicator having an indexing mechanism (13, 43) actutable by movement of the container (2) relative to the housing (1). The indexing mechanism (13, 43) includes a coupling element to compensate for excess movement of the container (2) relative to the housing (1).

25 Claims, 7 Drawing Sheets

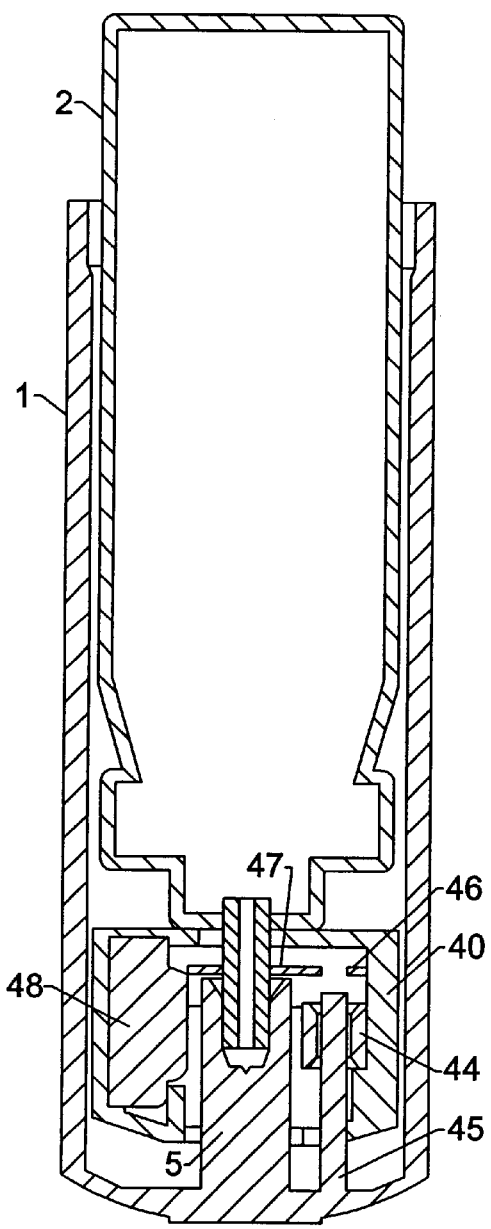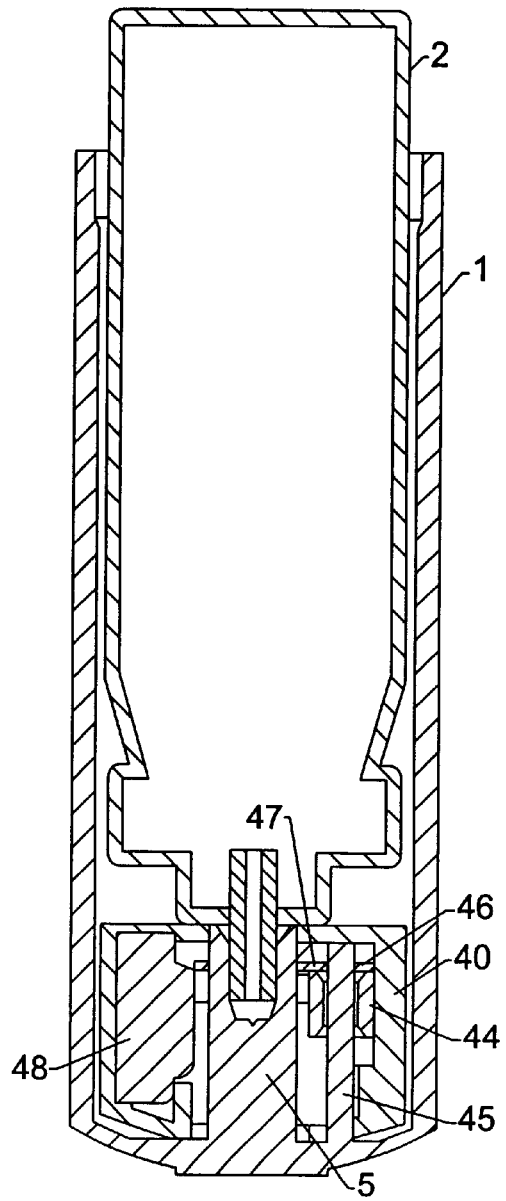

DISPENSER WITH DOSES COUNTER

The present invention relates to a dispenser having an actuation indicating device for indicating the number of actuations thereof. In particular, the invention relates to metered dose inhalers by means of which medicaments contained in an aerosol container may be administered to a patient.

It is well known to treat patients with medicaments contained in an aerosol, for example, in bronchodilator therapy. It is also known to use for such therapy, medicaments which are contained in an aerosol and are administered to a patient by means of an inhalation device comprising a tubular housing or sleeve in which the aerosol container is located and an outlet tube leading out of the tubular housing. The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the housing is then held by the patient in a more or less upright condition and the mouthpiece or nozzle of the inhalation device is placed in the mouth or nose of the patient. The aerosol container is pressed towards the support to dispense a dose of medicament from the container which is then inhaled by the patient.

A problem arising from use of such known devices is that the patient cannot determine the amount of medicament in the container at any given time. In an extreme case this could mean that the patient, possibly suffering from severe bronchospasm and needing a dose of medicament, will find that the container will not dispense a dose because its contents have already been exhausted.

In solution to the above described problem there has been suggested the use of dose indicating devices, which typically count the number of doses delivered from or remaining in the aerosol container, thereby enabling the patient to determine how much medicament is available in the container for future use. Typically, the dose indicating device has an indexing (i.e. counting) mechanism actuated by movement of the container relative to the housing, wherein a preset amount of relative movement results in a count being indexed.

U.S. Pat. No. 4,817,822 describes an aerosol dispenser having a dose indicating device which, in a first embodiment is removably attached to the end of the protruding portion of the aerosol container. The operating mechanism of the dose counter is located within a housing which extends from the end of the aerosol container along the external surface of the tubular housing.

U.S. Pat. No. 4,817,822 describes a dispenser having a dose indicating device in which the operating mechanism of the dose indicating device is located within a compartment in the housing and is actuated by means of an actuator member attached to the aerosol container.

WO96/16686 describes an aerosol dispenser wherein the operating mechanism of the dose indicating device is electronic and wherein the actuating member comprises a microswitch set into the wall of the housing. The electronic counting mechanism and microswitch are contained within a hermetically sealed enclosure.

U.S. Pat. No. 5,482,030 describes an aerosol dispenser having a mechanical dose indicator device located in and connected to the housing in the vicinity of the outlet tube of the aerosol container when fitted.

Many different pharmaceutical products are sold in the form of aerosol containers requiring different sized container bodies and/or valves according to the required specifications. It is therefore normal for there to be dimensional variations between different aerosol containers. Even between the same products the re can be dimensional variations due to manufacturing tolerances.

A problem which is common to all of the dose indicating devices discussed above is that the indexing mechanism, which is actuated by relative movement between the container body and housing, lacks any means of compensating for dimensional variations between different aerosol containers. Hence, the indexing mechanisms must be dimensioned according to the product with which they are to be used, and so will not be interchangeable with other products. Furthermore, in order for the indexing mechanism to record a count accurately, the dimensions of the components of any particular device must be manufactured to the required high tolerances.

The Applicants have now found that this problem can be ameliorated by use of a coupling element which compensates for excess movement (i.e. overtravel) of the container relative to the housing. By excess movement herein it is meant movement greater than that required to index a count. In one aspect, such excess movement is related to dimensional variations in the container and other parts of the dispenser.

According to one aspect of the present invention there is provided a dispenser comprising a housing having a support; a container, locatable within said housing, having an outlet, wherein said container dispenses through said outlet in response to movement of the container relative to the housing; and an actuation indicator having an indexing mechanism actuatable by movement of the container relative to the housing, wherein the indexing mechanism includes a coupling element to compensate for excess movement of the container relative to the housing.

By use of coupling element, such as a lost motion coupling, it is possible to create an actuation indicator of one size which can be used in dispensers having valves and actuators made within a wide range of manufacturing tolerances and can even fit a range of valves and actuators made to different dimensions.

Suitably, the indexing mechanism is actuatable by a predetermined movement of the container relative to the housing.

Suitably, the indexing mechanism indexes actuation by means of a predetermined rotary movement of a first member driven by movement relative to a second member during actuation of the dispenser. Preferably, the second member remains stationary relative to the housing during actuation of the dispenser.

In one preferred aspect, the first member comprises a pinion carried by a shaft through the coupling element and the second member comprises a rack.

In another preferred aspect, the first member comprises a yoke for engagement with the second member through the coupling element.

Suitably, the coupling element comprises a friction drive mechanism.

Suitably, the container is an aerosol container.

Suitably, the container provides measured doses. Preferably, the actuation indicator indicates the number of doses dispensed from or remaining in the container.

Suitably, the dispenser herein comprises a housing having a support; a container, locatable within said housing, having an outlet member, wherein said container is movable relative to the housing to enable dispensing therefrom and said outlet member is connectable with said support to prevent relative movement therebetween; and an actuation indicator, locatable within said housing. Preferably, the container and actuation indicator are reversably removable from the housing as a single unit.

Suitably, the actuation indicator is engagable with the container in the vicinity of the outlet member. More preferably, the actuation indicator is engagable with the outlet member.

Suitably, the actuation indicator is provided with a grip member which is engagable with a neck portion of the container. Preferably, the neck portion is adjacent to or on the outlet member.

Suitably, the housing is provided with an outlet, more preferably in the form of a mouthpiece. Preferably, the dispenser comprises a passage through which dispensed doses may pass from the container to the outlet.

Suitably, the dispenser is a breath operated inhaler which is actuable in response to the inward breath of a user.

Preferably, the dispenser herein is an aerosol dispenser comprising a housing in which a container is removably located, an outlet leading from the housing and a support in the housing arranged to receive an outlet member of the container and having a passage through which the contents of the container may pass to the outlet, the outlet member being held stationary in the housing support and the body of the container being moveable relative to the outlet and housing to dispense its contents in measured doses, and an actuation indicating device having an actuation indicator for indicating the number of doses dispensed from or remaining in the container. More preferably, the actuation indicating device is tightly connected to the container in the vicinity of the outlet member, such that the container and actuation indicating device may be removed from the housing as a single unit.

Preferably, the dispenser herein is a metered dose inhaler comprising a housing in which the container is removably located, an outlet leading from the housing, a support in the housing arranged to receive the outlet member of the container and having a passage through which the contents of the container may pass to the outlet, the outlet member being held stationary in the housing support and the body of the container being movable relative to the outlet and housing to dispense its contents in measured doses, and a window through which the actuation indicator may be viewed.

A dispenser according to the invention will now be described with reference to the accompanying drawings in which:

FIG. 8 shows a schematic section through an inhalation device comprising the dose indicating device of FIG. 6 in a rest position; and FIG. 9 shows a schematic section through the inhalation device of FIG. 8 in an actuated position.

Figure 1:
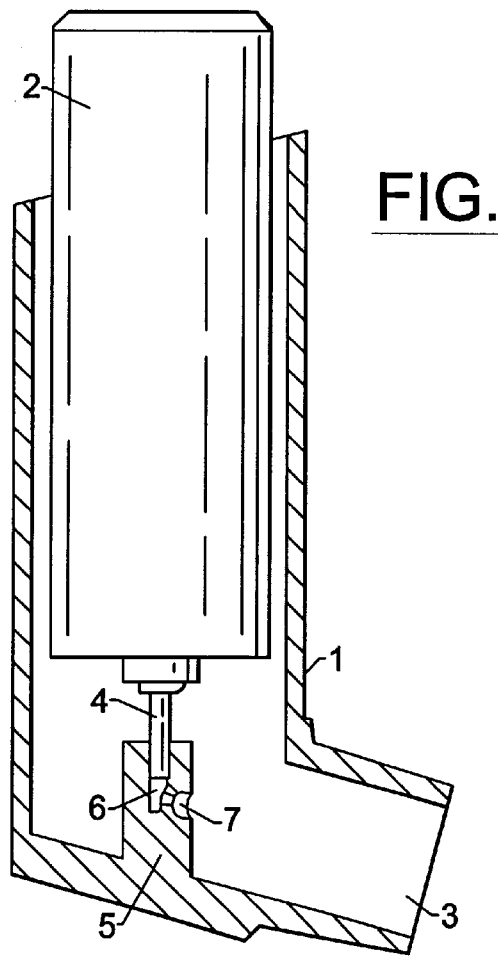
FIG. 1 is a section through a standard inhalation device comprising an aerosol dispenser.

A standard metered dose inhaler shown in FIG. 1 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril.

The aerosol container 2 has an outlet valve stem 4 at one end. This valve member can be depressed to release a measured dose from the aerosol container or, alternatively, the valve stem 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the container 2 spaced from the internal surface of the housing 1. A support 5 is provided at the lower end of the housing 1 and has a passage 6 in which the valve stem 4 of the aerosol container 2 can be located and supported. A second passage 7 is provided in the support 5 and is directed towards the interior of the outlet 3. Thus, when the parts are in the positions shown in FIG. 1, the protruding portion of the aerosol container 2 can be depressed to move the container from its rest position relative to the valve stem 4 to open the valve and a dose of medicament contained in the aerosol will be discharged through the passage 7 and into the outlet 3 from which it can be inhaled by a patient. One dose will be released from the aerosol container each time it is fully depressed.

Figure 2:
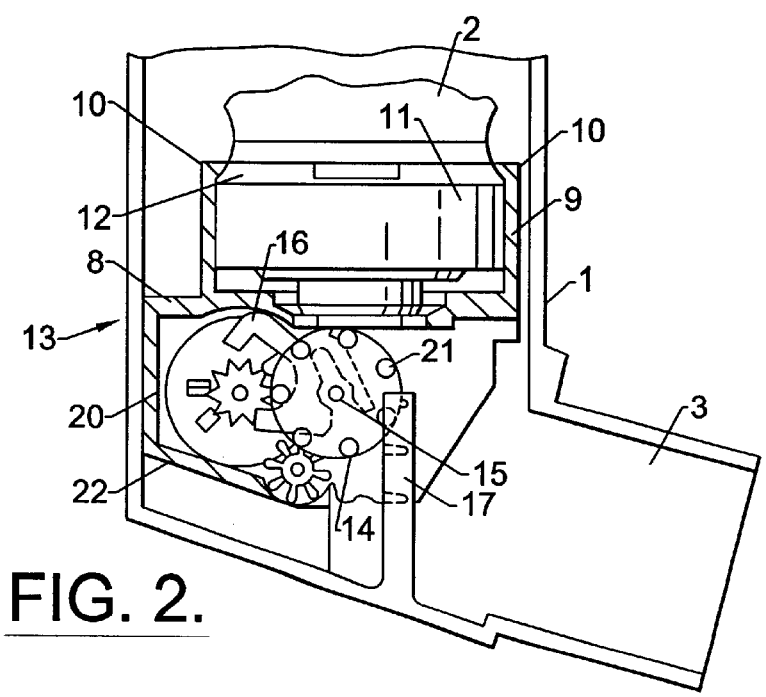
FIG. 2 is a section through the dose indicating device as fitted to an aerosol dispenser in an inhalation device.

FIG. 2 shows the lower part of a device similar to that of FIG. 1 but incorporating a dose indicating device according to the invention. The dose indicating device comprises a body 8 firmly attached to the aerosol container by means of tubular portion 9 formed with lip 10. Tubular portion 9 tightly engages the periphery of valve ferrule 11 while a grip in the form of lip 10 engages around neck 12 of valve ferrule 11 which is formed during assembly when valve ferrule 11 is crimped onto aerosol container 2. Thus the tubular portion 9 and lip 10 form a tight connection to the aerosol container which once assembled by pushing the tubular portion 9 over the valve ferrule 11 cannot easily be dissembled.

Below tubular portion 9, body 8 forms a cradle 22 for mounting counter mechanism 13 and drive pinion 14. Drive pinion 14 is friction mounted on counter mechanism drive shaft 15. Drive pinion 14 is formed with a number of teeth or pegs 21 which can engage with a number of recesses or grooves formed on post 17 in the form of a rack moulded inside housing 1 and extending from the base of the housing 1 parallel to valve stem 4.

Figure 3:
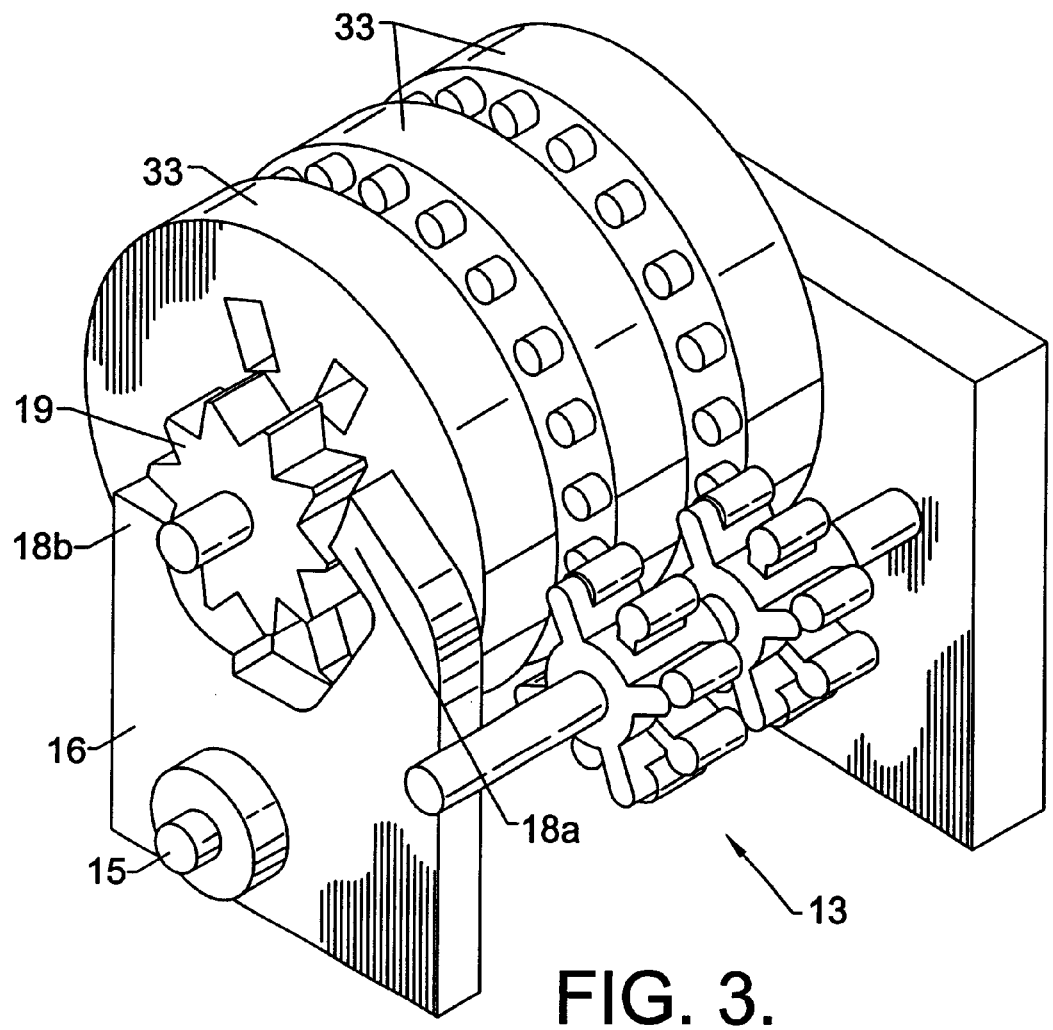
FIG. 3 is a perspective view of a counting mechanism used in the dose indicating device of FIG. 2.
Figure 4A:
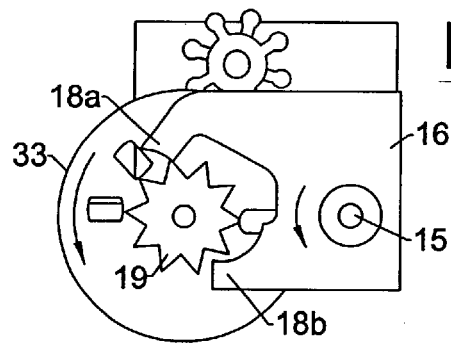
FIG. 4 shows the sequence of operation of the counter mechanism of FIG. 3.
Figure 4B:
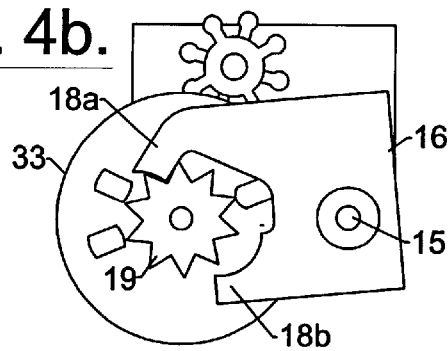
Figure 4C:
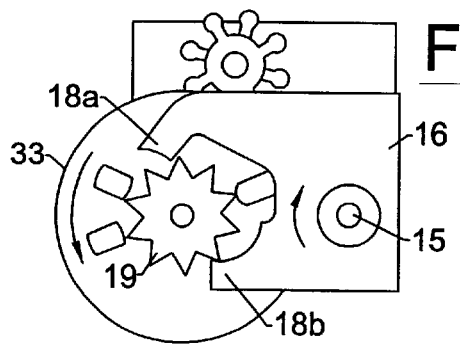
Figure 4D:
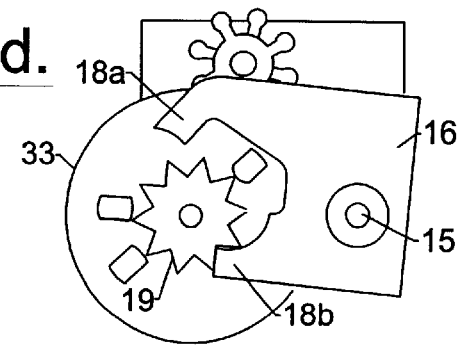
Figure 5A:
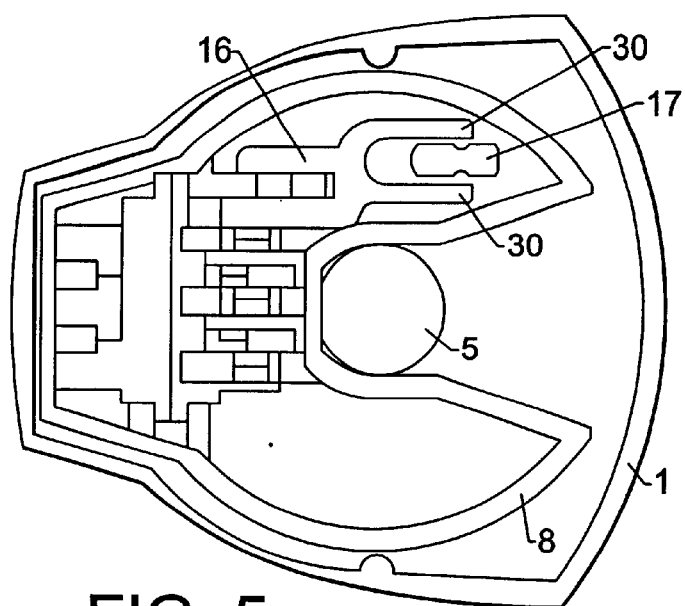
FIG. 5 shows a lateral and a longitudinal section through a second embodiment of the dose indicating device as fitted into the housing of an inhalation device.
Figure 5B:
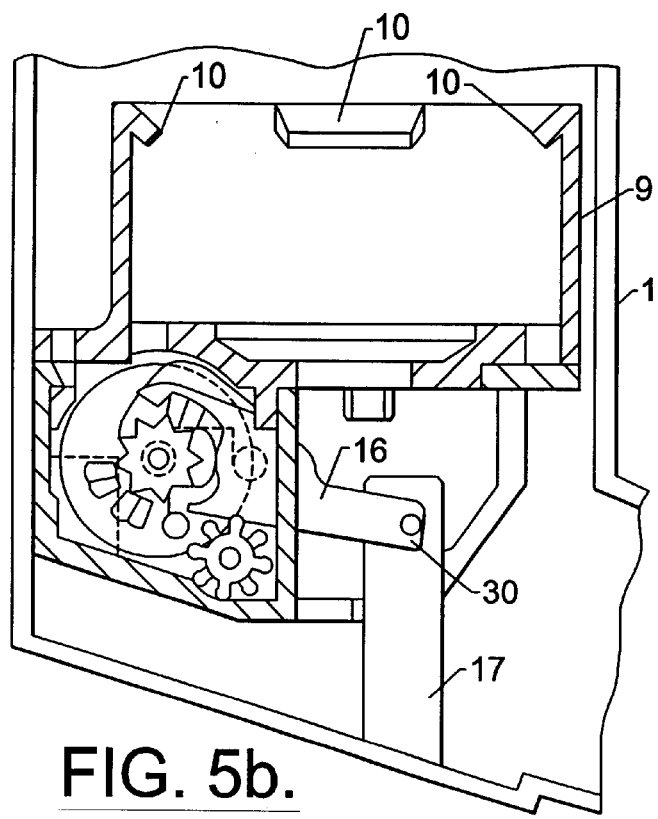
Figure 6:
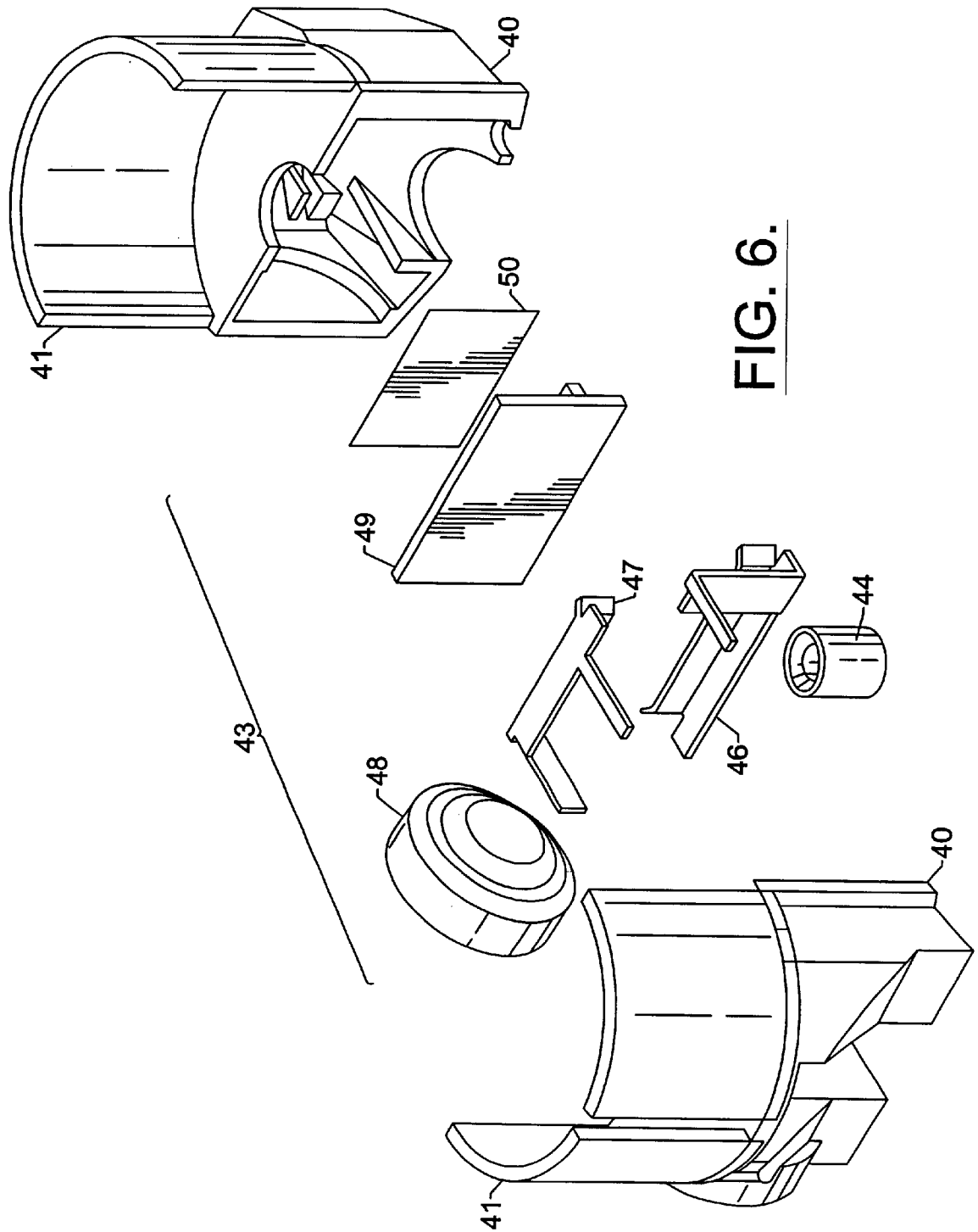
FIG. 6 shows an exploded view of a dose indicating device according to a third embodiment of the invention.

As shown in FIGS. 3 and 4, drive shaft 15 is connected to driver yoke 16 of counter mechanism 13. Driver yoke 16 has two switching latches 18a and 18b spaced either side of star wheel 19 such that driver yoke 16 may tilt about the axis of drive shaft 15 between a first position shown in FIG. 4b in which switching latch 18a engages one side of star wheel 19, and a second position shown in FIG. 4d in which switching latch 18b engages the other side of star wheel 19.

Star wheel 19 is connected through a mechanism, similar to that described with reference to reference numerals 2 to 8 in FIGS. 1 to 3 of European Patent No. 0280104, to three digit wheels 33, which have numbers printed on their circumferential faces as described below. When located in the housing 1, counter mechanism 13 is small enough to be located to the sides of and behind support 5 so as not to interfere with the aerosol flume as it emerges from passage 7.

The aerosol container 2 may be supplied to the patient with the dose indicating device ready assembled thereto. Alternatively, the housing 1 may be supplied to the patient with the dose indicating device located in the position shown in FIG. 2 and the aerosol container 2 supplied separately. In this case, the patient is instructed to insert the aerosol container 2 into the housing 1 with the valve stem first. Upon first insertion of the container into the housing, the tubular portion 9 and lip 10 of the dose indicating device ride over the periphery of valve ferrule 11 of the aerosol container 2 until lip 10 snaps around neck 12. Thereafter, the dose indicating device is attached to the aerosol container 2.

Other means of attachment of the dose indicator to the container are envisaged including adhesive attachment; use of welded shrink sleeves; heat forming; crimping; ultrasonic welding; and by the presence of an o-ring elastomer on the container which is fixedly piercable by barbs on the attachment member of the dose indicator.

To actuate the device, the protruding portion of the aerosol container is depressed as described above with reference to FIG. 1. As the aerosol container carrying the dose indicating mechanism moves within housing 1, drive pinion 14 starts to turn, through its engagement with post 17, causing rotation of drive shaft 15 and driver yoke 16. As driver yoke 16 tilts with rotation of drive shaft 15 switching latch 18*a* moves into engagement with star wheel 19 (FIG. 4*a*) causing an incremental anti-clockwise rotation of a half tooth pitch of the star wheel until the switching latch 18a can move no further in this direction, the switching latch being positioned between two adjacent teeth of the star wheel (FIG. 4*b*). At this point, drive shaft 15 cannot rotate any further and any further movement of the aerosol container into housing 1 results in drive pinion 14 continuing to rotate through its engagement with post 17 by virtue of the friction coupling between pinion 14 and drive shaft 15.

When the valve stem 4 has reached its fully depressed position and a metered dose of medicament has been discharged from the aerosol container, the aerosol container is allowed to return to its original position. As the aerosol container and dose indicating mechanism return to their original position, drive pinion 14 starts to rotate in the opposite direction together with drive shaft 15 and driver yoke 16. Thus, driver yoke 16 tilts such that switching latch 18a moves out of engagement with star wheel 19 while switching latch 18b moves into engagement therewith (FIG. 4*c*), causing further incremental anti-clockwise rotation of a half tooth pitch of the star wheel until switching latch 18*b* can move no further in this direction (FIG. 4*d*). Again, drive shaft 15 cannot rotate any further at this point and any further movement of the aerosol container out of housing 1 results in drive pinion 14 continuing to rotate through its engagement with post 17 by virtue of the friction coupling between pinion 14 and drive shaft 15. In this way it can be seen that the friction coupling acts as a lost motion coupling which allows the dose indicating device to be used with aerosol containers having valves with different lengths of travel of valve stem during actuation.

Each time the aerosol dispenser is actuated the star wheel is made to rotate through two incremental anti-clockwise movements as described above. These movements are translated through the counter mechanism into appropriate movements of the digit wheels 33, one number on each of the printed circumferential faces of the digit wheels being clearly visible through the window 20 at the back of the housing 1 (as shown in FIG. 2), to indicate that a further dose of medicament has been dispensed. By having three digit wheels 33 it is possible for the dose counter to be used to count hundreds of doses. Clearly if fewer than one hundred doses are to be contained within the dispenser, the dose counter could comprise fewer digit wheels. Alternatively, if a thousand or more doses are to be contained, then one or more additional digit wheels could be added as appropriate.

To remove the aerosol container 2 from the housing for cleaning, the aerosol container 2 may be withdrawn from the housing 1 in the usual manner. As the container is withdrawn, the friction coupling between drive pinion 14 and drive shaft 15 allows such further movement as is required for the drive pinion to come out of engagement with the post 17 without causing any further indexing of the counter mechanism. Once removed, the housing 1 may be cleaned as described without fear of interfering with or damaging the dose indicating device, which remains firmly connected to the aerosol container 2.

When the housing 1 is clean, the aerosol container 2 with dose indicating device may be re-inserted into the housing 1. During insertion, drive pinion 14 will engage post 17 and start to rotate until the aerosol container reaches its normal rest position with the valve stem 4 located in support 5. As the drive pinion 14 rotates, the friction coupling will act as a lost motion mechanism as described above, allowing for any travel of the aerosol container as between first engagement of drive pinion 14 and post 17, and location of valve stem 14 in support 5. In this way, the friction coupling automatically accommodates and compensates for different lengths of valve stems protruding from the ferrule.

FIG. 5 shows an alternative lost motion coupling mechanism which may be used in an aerosol dispenser according to the invention. In this embodiment, instead of a pinion, driver yoke 16 is formed with two resilient arms 30 between which post 17 is grippingly engaged (FIG. 5*a*). Post 17 is formed with ribs on its surface (not shown) which provide a rough surface finish to create the level of friction required between arms 30 and post 17 such that arms 30 will grip post 17 until the load applied overcomes the friction.

Upon actuation of the device, as the aerosol container and dose indicating mechanism move, the friction engagement between arms 30 and post 17 cause driver yoke 16 to tilt about the axis of shaft 15 (not shown in FIG. 5), so moving switching latch 18*a* into engagement with star wheel 19 as discussed in relation to the first embodiment. As switching latch 18a reaches its limit of travel, driver yoke 16 can move no further, and any further movement of the aerosol container into housing 1 results in arms 30 slipping down post 17 by virtue of the friction coupling. Upon return to its original position, driver yoke 16 tilts in the other direction until switching latch 18b moves into engagement with star wheel 19 and can move no further. Any further movement of the aerosol container out of housing 1 results in arms 30 slipping up post 17.

FIGS. 6 to 9 show an inhalation device fitted with an electro-mechanical dose indicating device according to the invention. As with the mechanical embodiments discussed above, the dose indicating device comprises a body 40 firmly attached to the aerosol container by means of tubular portion 41 formed with grips (not shown). Tubular portion 41 tightly engages the periphery of valve ferrule 11 while a grip in the form of a lip engages around neck 12 of valve ferrule 11. Thus the tubular portion 41 and lip form a tight connection to the aerosol container which once assembled by pushing the tubular portion 41 over the valve ferrule 11 cannot easily be disassembled.

Below tubular portion 41, body 40 forms a cradle for mounting counter mechanism 43, and defines a chamber for accommodating switch slide 44. Switch slide 44 is a cylindrical washer made of silicone rubber and having a bore of such a diameter that, with the can and dose indicating device mounted within the actuator housing, it provides a friction fit on pin 45, which is moulded in the housing and protrudes through a hole in body 40. The friction fit of switch slide 44 on pin 45 ensures the switch slide will not move along the pin unless pushed. Two contact members 46, 47, both of which comprise a switch contact and a circuit board contact, and one of which further comprises a battery contact, are mounted such that the battery and circuit board contacts are in constant contact with a first terminal of the battery 48 and printed circuit board (PCB) 49 respectively. The switch contacts do not contact each other but are positioned either side of pin 45, and define the upper limit of movement of the switch slide 44 within its chamber. Thus, when switch slide 44 is in its upper position as shown in FIG. 9, it makes contact with both switch contacts, so closing the circuit between them due to the electrical conductivity of the silicone rubber of the switch slide. Although in the embodiment described the switch slide is made of silicone rubber, it will be appreciated that it could alternatively be made of a non-conductive rubber having an insert at its upper face made of metal or some other conductive material.

In addition to its connections with contact members 46, 47, PCB 49 also has connections to the other terminal of the battery and to a three digit liquid crystal display (LCD) 50 in a conventional manner. The PCB comprises an application specific integrated circuit (ASIC), which provides the logic by which the dose indicator can be checked, programmed and made operational, as discussed in more detail below. to keep a record of how many times the switch contact circuit is closed and drives the LCD to display the number of doses remaining in the aerosol container. The ASIC is thus designed and programmed accordingly In a known manner.

Figure 7:
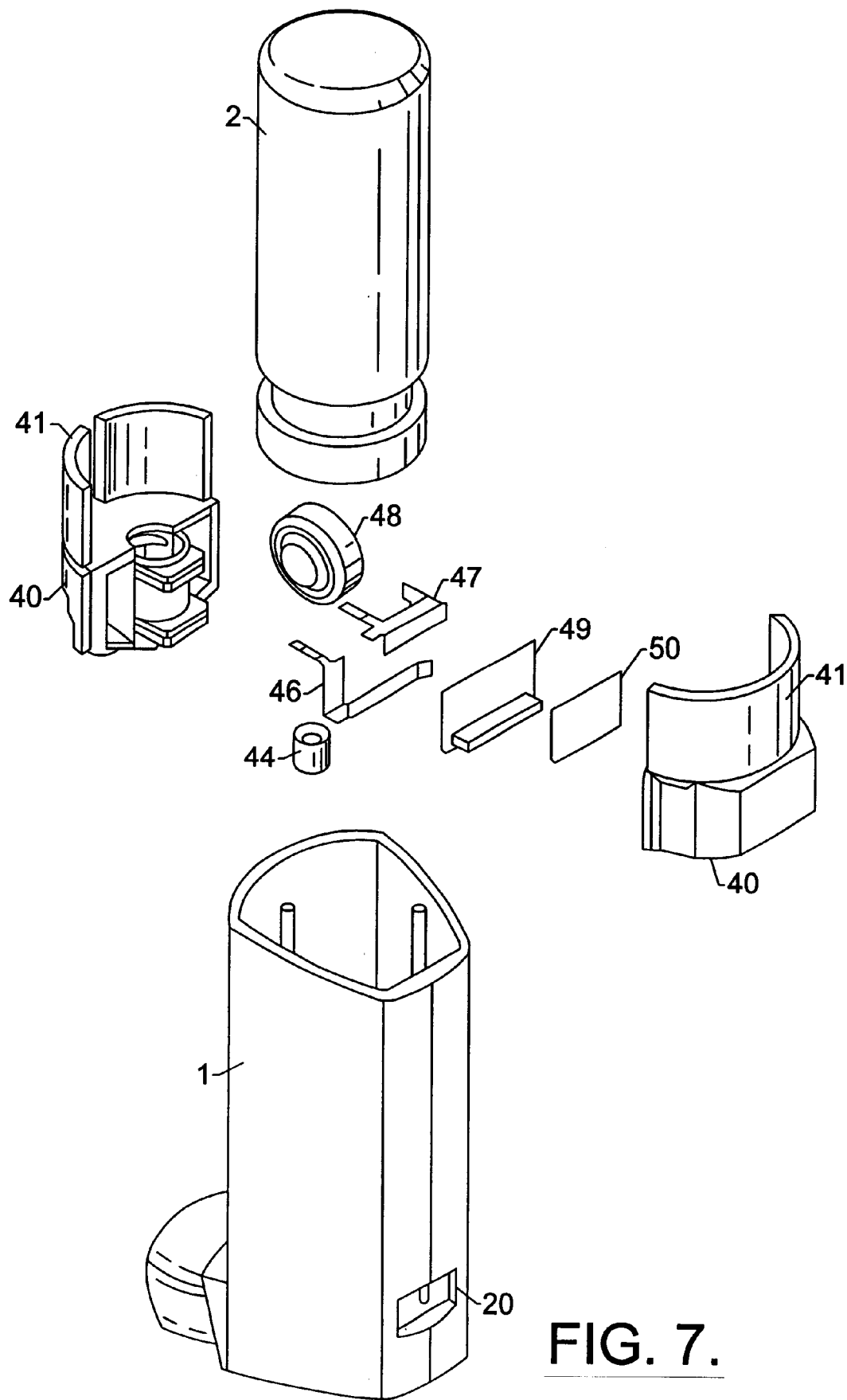
FIG. 7 shows another exploded view of the dose indicating device of FIG. 6 together with an aerosol container and housing.

Instead of a digital display, the LCD could alternatively be formatted to display an analogue indication. W h e n the aerosol container is mounted in the actuator housing, LCD 50 is visible through window 20. In the embodiment depicted in FIG. 7, the LCD and window are located at the back of the housing, but they could equally be located at the front or some other part of the housing.

The Counter mechanism 43 is small enough to be located to the sides of and behind the stem block (support 5) moulded in housing so as not to interfere with the aerosol flume as it emerges.

To actuate the device, the protruding portion of the aerosol container when fitted into the actuator housing is depressed as described above. As the aerosol container carrying the dose indicating mechanism moves within the housing from its rest position (shown in FIG. 8), the chamber accommodating switch slide 44 moves down until the upper face of switch slide 44, which is mounted on pin 45, meets switch contacts 46, 47 and the switch circuit is closed. This causes the ASIC to decrement the number displayed by the LCD 50. As the aerosol container continue s to move, a metered dose of medicament is discharged from the valve, while switch slide 44 is pushed down along pin 45 by virtue of the friction fit of the switch slid e o n the pin until the valve stem reaches its limit of travel and the aerosol container moves no further (FIG. 9). In this way, it can be seen that the friction fit of the switch slide 44 on pin 45 allows for over-travel of the valve stem after the switch circuit has been closed, so acting as a lost motion coupling. The aerosol container is then allowed to return to its original position within the housing, and as it returns, the chamber accommodating switch slide 44 moves up breaking the switch circuit as switch contacts 46, 47 move away from switch slide 44. Body 40 then meets the lower face of switch slide 44 and draws the switch slide up along pin 45 until the valve stem returns to its rest position (FIG. 8).

Because the dose indicating device is designed to be suitable for use in connection with different sized aerosol containers containing different numbers of doses to be delivered, the ASIC is designed to be factory set in accordance with the size of aerosol container with which the dose indicating device is assembled. After assembly of the dose indicating device and first connection of the battery, the ASIC enters a self-test mode. After this, the programming mode may be entered by activating the switch, allowing it to be programmed to count down from the appropriate number of doses (e.g. 200, 120, 80 or 60). This may be done automatically on a packing line. After programming has taken place, the ASIC enters the counting mode, where the LCD decrements upon closing of the switch contact circuit. When the count of zero is reached, the ASIC is designed to prevent the count from decrementing any further in a known manner. In order to prevent spurious readings due to the effects of switch 'bounce', the ASIC may be designed to decrement only after the switch circuit has been closed for a predetermined length of time in a known manner. In the event of the aerosol container getting jammed in the actuated position after operation, or the switch circuit jamming closed due to mechanical damage or contamination, the ASIC may be designed to blank the LCD to alert the user that there is a problem.

As with the other embodiments of the invention described above, the aerosol container may be withdrawn from the actuator housing in the usual manner. As the container is withdrawn, body 40 draws the switch slide up along pin 45 until it clears the pin altogether. Once removed, the housing may be cleaned without interfering with or damaging the dose indicating device, which remains firmly connected to the aerosol container.

During re-insertion of the aerosol container, which can only occur when the body of the dose indicating device is correctly orientated with respect to the housing by virtue of their respective shapes, switch slide 44 engages and is pushed up by pin 45 until the upper face meets the switch contacts. Further insertion of the aerosol container results in switch slide 44 being pushed down along pin 45 until the valve stem is seated back within support 5.

It will be appreciated that by programming of the ASIC, one design of dose indicating device could be used in conjunction with a range of aerosol containers of various capacities. By virtue of the switch mechanism, the same design of dose indicating device can also be used in conjunction with a range of different valves having different lengths of valve stem and different stem travel specifications.

Whilst the present invention has been described in detail in respect of a metered dose inhaler actuatable manually by the patient it will be appreciated that other actuation mechanisms can be substituted. In particular, the use of a breath operated inhaler in which the actuation is assisted, and is responsive to, preferably triggered by, the inward breath of the patient, is also envisaged.

The dispenser of the invention is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3,5-dichloro-α-[[[6-[2-(2-pyridinyl)ethoxy] hexyl]methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, saimeterol, fluticasone propionate and beclometasone dippropionate and salts or sovates thereof, e.g., the sulphate of albuterol and the xinafoate of saimeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A drug product comprising:
   a housing having a support;
   a container containing a drug formulation comprising a medicament and a propellant, locatable within said housing, having an outlet, wherein said container is actuable; and
   an actuation indicator engaging the container including a drive shaft frictionally coupled to a pinion, a post engaging the pinion, a yoke engaging the drive shaft, and first and second switching latches engaging a star wheel,
   wherein the drive shaft, yoke, and pinion each rotate in a plane longitudinal to movement of the container.

2. A drug product according to claim 1, wherein the actuation indicator is actuatable by a predetermined movement of the container relative to the housing.

3. A drug product according to claim 1, wherein the pinion rotates relative to a rack during actuation of the dispenser.

4. A drug product according to claim 3, wherein the rack remains stationary relative to the housing during actuation.

5. A drug product according to claim 1, wherein the pinion frictionally coupled to the shaft accommodates a plurality of valve stems of different length.

6. A drug product according to claim 1 wherein the container is an aerosol container including a valve having a valve stem.

7. A drug product according to claim 1 wherein said container provides measured doses of the drug formulation including the medicament and the propellant.

8. A drug product according to claim 7 wherein said actuation indicator indicates the number of doses of medicament dispensed from or remaining in the container.

9. A drug product according to claim 1, actuable in response to the inward breath of a user.

10. A method of delivering a medicament to a patient comprising administering the medicament to the patient by actuating the drug product according to claim 1.

11. A drug product comprising:
   an aerosol canister including a can containing a propellant and a medicament, and a valve having a valve stem;
   an actuator removably engaging the aerosol canister; and,
   an actuation indicator engaging the aerosol canister including a drive shaft frictionally coupled to a pinion, a post engaging the pinion, a yoke engaging the drive shaft, and, first and second switching latches engaging a star wheel,
   wherein the drive shaft, yoke, and pinion each rotate in a plane longitudinal to movement of the aerosol canister.

12. The drug product of claim 11, wherein the medicament is selected from the group consisting of beclomethasone, fluticasone, flunisolide, budesonide, rofleponide, mometasone, triamcinolone, noscapine, albuterol, salmeterol, ephedrine, adrenaline, fenoterol, formoterol, isoprenaline, metaproterenol, terbutaline, tiotropium, ipratropium, phenylephrine, phenylpropanolamine, pirbuterol, reproterol, rimiterol, isoetharine, tulobuterol, (−)-4-amino-3,5-dichloro-α-{{{6-{2-(2-pyridinyl)ethoxy}hexyl}methyl} benzenemethanol, esters, solvates and salts thereof, and combinations thereof.

13. The drug product of claim 12, wherein the medicament is albuterol sulphate.

14. The drug product of claim 12, wherein the medicament is salmeterol xinafoate.

15. The drug product of claim 12, wherein the medicament is fluticasone propionate.

16. The drug product of claim 12, wherein the medicament is beclomethasone dipropionate.

17. The drug product of claim 12, wherein the medicament is the combination of salmeterol xinafoate and fluticasone propionate.

18. The drug product of claim 12, wherein the medicament is salmeterol xinafoate and a salt, ester or solvate of ipratropium.

19. The drug product of claim 12, wherein the aerosol canister includes a ferrule; wherein the actuator includes a body housing the actuation indicator; and, wherein the actuation indicator includes a tubular member to receive the ferrule.

20. The drug product of claim 19, wherein the actuator further includes a window to display numerals on one or more digit wheels engaging the star wheel.

21. The drug product of claim 19 comprising 3 digit wheels each having numerals 0 through 9.

22. A drug product comprising:

means for containing a drug formulation comprising a medicament and a propellant;

means for metering the drug formulation engaging the containing means;

means for actuating the metering means;

means for supporting the metering means and containing means;

means for indicating actuation engaging the containing means and metering means; and, means for housing the containing means, metering means, support means and actuation indicating means.

23. A drug product comprising:

means for containing a drug formulation comprising a propellant and a medicament;

means for metering the drug formulation engaging the containing means;

means for actuating the metering means;

means for indicating actuation engaging the containing means and metering means.

24. A method of treating a patient comprising:

providing the drug product of claim 12;

actuating the drug formulation into the lungs of a patient; and, indexing the actuation indicator.

25. A method of treating a patient comprising:

providing the drug product of claim 1;

actuating the drug formulation into the lungs of the patient; and, indexing the actuation indicator.

* * * * *